US005610283A

United States Patent [19]

Buechler

[11] Patent Number: 5,610,283
[45] Date of Patent: Mar. 11, 1997

[54] OPIATE DERIVATIVES AND PROTEIN AND POLYPEPTIDE OPIATE DERIVATIVE CONJUGATES AND LABELS

[75] Inventor: Kenneth F. Buechler, San Diego, Calif.

[73] Assignee: Biosite Diagnostics Incorporated, San Diego, Calif.

[21] Appl. No.: 389,969

[22] Filed: Feb. 15, 1995

Related U.S. Application Data

[63] Continuation of Ser. No. 864,107, Apr. 6, 1992, abandoned.
[51] Int. Cl.$^6$ .......... C07K 17/02; C07D 489/02; C07H 17/00; A61K 39/385
[52] U.S. Cl. .......... 530/404; 530/408; 536/17.4; 546/44; 436/543; 436/816; 435/961; 435/188
[58] Field of Search .......... 530/404, 408; 435/964, 961, 188; 436/501, 543, 544, 816, 822, 824, 901; 546/64; 536/17.4

[56] References Cited

U.S. PATENT DOCUMENTS

| | | | |
|---|---|---|---|
| 3,852,157 | 12/1974 | Rubenstein et al. | 435/7.8 |
| 3,884,898 | 5/1975 | Schneider | 530/363 |
| 4,231,999 | 11/1980 | Carlsson et al. | 435/7.9 |
| 4,232,119 | 11/1980 | Carlsson et al. | 435/7.9 |
| 4,695,624 | 9/1987 | Marburg et al. | 530/404 |
| 4,939,264 | 7/1990 | Heiman et al. | 436/537 |

FOREIGN PATENT DOCUMENTS

| | | |
|---|---|---|
| 0254120 | 7/1984 | European Pat. Off. ...... C07D 489/00 |
| 9218866 | 10/1992 | WIPO . |

OTHER PUBLICATIONS

Rowley et al J. Biol. Chem. (1975) 250(10): 3759–3766.
Colbert et al (1988) J. Immunoassay 9(3 & 4): 367–383.
Blair et al (1983) J. Immunol. Methods 59:129–143.
Jung et al (1981) Biochem. Biophys. Res. Commun. 101(2): 599–604.

Cone, Edward J. et al., Forensic Drug Testing for Opiates: IV. Analytical, Sensitivity, Specificity and Accuracy of Commercial Urine Opiate Immunoassays, J. Anal. Tox. 16:72–78 (1992).
Cone, Edward J. et al., Forensic Drug Testing for Opiates:I. Detection of 6–Acetylmorphine in Urine as an Indicator of Recent Heroin Exposure; Drug and Assay Considerations and Detection Times, J. Anal. Tox. 15:1–7 (1991).
Kaiser, Carl et al., Sigma Receptor Ligands: Function and Activity, Neurotransmissions: 7: No. 1 1–8 (1991).
McKnight, Alexander and Rees, David C. Neurotransmissions: 7: No. 2 1–8 (1991).
Ram, Vishnu J. and Neumeyer, John L., Aporphines, 42. Synthesis of (R)–(–D–11–Hydroxaporphines from Morphine, J. Org. Chem. 47:4372–74 (1982).
Krafft, Grant A., et al., Photoactivable Flurophones 3. Synthesis and Photoactivation of Flurogenic Difunctionalized Fluroescerns, J. Am. Chem. Soc. 110:301–03 (1989).
Rice, Kenner, C. and May Everette L., Procedural Refinements in the N–Demethylation of Morphine and Codeine Using Phenyl Chloroformate and Hydrazine, J. Heterocyclic Chem. 14:665–66 (1977).
Rice, Kenner, C. and Jacobson, Arthur E., Preparation and Analgesic Activity of 3,6–Diacetyl–normorphine and 6–Acetylnormorphine, J. Med. Chem. 18:1033–35 (1975).

(List continued on next page.)

*Primary Examiner*—Kay K. A. Kim
*Attorney, Agent, or Firm*—Lyon & Lyon

[57] ABSTRACT

The present invention is directed to novel opiate derivatives which are synthesized for the covalent attachment to antigens (proteins or polypeptides) for the preparation of antibodies or receptors to the opiates and opiate metabolites. The resulting novel antigens may be used for the production of antibodies or receptors using standard methods. Once generated, the antibodies or receptors and the novel derivatives which are covalently attached to proteins, polypeptides or labels may be used in the immunoassay process.

5 Claims, 4 Drawing Sheets

EXAMPLE 9

EXAMPLE 10

EXAMPLE 11

EXAMPLE 12

OTHER PUBLICATIONS

Weijlard, John and Erickson, A. E., N–Allylnormorphine JACS 64:869–70 (1942).

Brine, George A. et al., the N–Demethylation of Morphone and Codeine Using Methyl Chloroformate, Organic Preparations and Procedures, Int. 8:103–106 (1975).

Kosterlitz, H. W. et al., the assay of the agonist activities of N–methyl and N–nor–homologies of morphine derivatives by the guinea pig ileum method, J. Pharm. Pharmac. 28:325 (1976).

Rice, Kenner C., An improved Procedure for the N–Demethylation of 6,7–Benzo morphines, Morphine, and Codeine, J. Org. Chem. 40:1850–51 (1975).

Speyer, Edmund and Walther L. Uberdie Einwirkung von Sulpetriger Säure auf Morphium und Seine Derivate, Ber. 63:852–855 (1930).

J. V. Braun, Untersuchungen uber Morphium Alka, Ber. 47:2312–2331 (1914).

EXAMPLE 1

EXAMPLE 2

EXAMPLE 3

EXAMPLE 4

EXAMPLE 5

EXAMPLE 6

EXAMPLE 7

EXAMPLE 9

EXAMPLE 10

EXAMPLE 11

EXAMPLE 12

EXAMPLE 13

EXAMPLE 14

EXAMPLE 15

EXAMPLE 16

OPIATE DERIVATIVES AND PROTEIN AND POLYPEPTIDE OPIATE DERIVATIVE CONJUGATES AND LABELS

This application is a continuation of application Ser. No. 07/864,107, filed Apr. 6, 1992, now abandoned.

FIELD OF THE INVENTION

This invention is in the field of ligand receptor assays, including immunoassays, for the detection of selected metabolites of opiates in a fluid sample. More particularly, this invention relates to methods for the synthesis of novel opiate derivatives and protein and polypeptide opiate derivative conjugates and labels for use in the preparation of antibodies to opiates and opiate metabolites and for use in the immunoassay process.

BACKGROUND OF THE INVENTION

Opiates are a class of alkaloids produced by plants of the poppy family. The most common opiates produced by the poppy plants are morphine and codeine. These opiates have been used for centuries to prevent pain but their continual use leads to addiction. Synthetic analogues of morphine also exhibit the narcotic and addictive properties of the natural opiates and include heroin (diacetylmorphine), hydromorphone, hydrocodone, levorphanol, oxycodone and oxymorphone. The illicit use of opiates, particularly heroin and morphine, has resulted in a medical need for antibodies and diagnostics to rapidly detect the opiate metabolites in order to monitor and treat opiate addiction.

The preparation of antibodies to the class of opiates and opiate metabolites requires the synthesis of an opiate derivative in order to covalently attach the derivative to an antigenic polypeptide or protein. In addition, the opiate derivative is covalently attached to various polypeptides, proteins or labels for use in screening antibodies and in the immunoassay process. The opiate derivative should mimic the structure of the opiate metabolite sought to be measured. Therefore, the selection and synthesis of the types of opiate derivatives for covalent attachment to proteins, polypeptides or labels is critical. In addition, the opiate derivatives need to be stable to hydrolysis in an aqueous solution.

Opiate compounds and conjugates for immunization and immunoassay have been described in U.S. Pat. Nos. 3,709,868, 3,852,157, 3,867,366, 3,884,898, 4,022,878, and in Science 176, 1143 (1972), and Science 178, 647 (1972).

SUMMARY OF THE INVENTION

The present invention is directed to novel opiate derivatives which are synthesized for the covalent attachment to antigens (proteins or polypeptides) for the preparation of antibodies to the opiates and opiate metabolites. The resulting novel antigens may be used for the production of antibodies using standard methods. Once generated, the antibodies and the novel derivatives which are covalently attached to proteins, polypeptides or labels may be used in the immunoassay process.

DEFINITIONS

In accordance with the present invention and as used herein, the following terms, are defined with the following meanings, unless explicitly stated otherwise.

"Drug" shall mean any compound or ligand which either as a result of spontaneous chemical reaction or by enzyme catalyzed or metabolic reaction, generates an intrinsic activity when administered to a biological system. The drug may be metabolized to a derivative of the drug by a biological system. Common examples of drugs and their metabolites are morphine, barbiturates, tetrahydrocarbinal, phencyclidine, amphetamines, methamphetamines, opiates, benzodiazepines, cocaine, estrone-3-glucuronide, pregnanediol-glucuronide, cotinine, lysergic acid diethylamide, propoxyphene, methadone, anabolic steroids and tricyclic anti-depressants.

"Drug derivative" shall mean a ligand derivative, drug, drug metabolite or a drug analogue conjugated to a linking group.

"Drug metabolite" shall mean a compound upstream or downstream from a drug in a biochemical or metabolic pathway, or an intermediate.

"Label" shall mean a signal development element or a means capable of generating a signal, for example, a dye or an enzyme. The attachment of a drug derivative to the label can be through covalent bonds, adsorption processes, hydrophobic and/or electrostatic bonds, as in chelates and the like, or combinations of these bonds and interactions.

"Opiate" shall mean any of the pentacyclic, naturally occurring alkaloids produced by the plants of the poppy family or the synthetic analogues of these alkaloids which include but are not limited to morphine, codeine, heroin, hydromorphone, hydrocodone, oxymorphone and the like.

"Binding domain" shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

"Linking group" shall mean the composition between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heteroatoms (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

"Hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain, cyclic structures or combinations thereof.

"Aryl" shall refer to aromatic groups which have at least one ring having a conjugated pi electron system and includes carbocyclic aryl, heterocyclic aryl and biaryl groups, all of which may be optionally substituted.

"Carbocyclic aryl groups" shall refer to groups wherein the ring atoms on the aromatic ring are carbon atoms. Carbocyclic aryl groups include monocyclic carbocyclic aryl groups and optionally substituted naphthyl groups.

"Monocyclic carbocyclic aryl" shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

"Optionally substituted naphthyl" shall refer to 1or 2-naphthyl or 1- or 2-naphthyl preferably substituted by lower alkyl, lower alkoxy or halogen.

"Heterocyclic aryl groups" shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

"Optionally substituted furanyl" shall refer to 2- or 3-furanyl or 2- or 3-furanyl preferably substituted by lower alkyl or halogen.

"Optionally substituted pyridyl" shall refer to 2-, 3- or 4-pyridyl or 2-, 3- or 4-pyridyl preferably substituted by lower alkyl or halogen.

"Optionally substituted thienyl" shall refer to 2- or 3-thienyl, or 2- or 3-thienyl preferably substituted by lower alkyl or halogen.

"Biaryl" shall refer to phenyl substituted by carbocyclic aryl or heterocyclic aryl as defined herein, ortho, meta or para to the point of attachment of the phenyl ring, advantageously para; biaryl is also represented as the —C$_6$H$_4$—Ar substituent where Ar is aryl.

"Aralkyl" shall refer to an alkyl group substituted with an aryl group. Suitable aralkyl groups include benzyl, picolyl, and the like, and may be optionally substituted.

"Lower" referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl —CO— or HCO—.

The terms "acylamino" refers to RCONCR)—and (RCO$_2$N—respectively, wherein each R is independently hydrogen or hydrocarbyl.

The term "hydrocarbyloxycarbonyloxy" shall refer to the group ROC(O)O—, wherein R is hydrocarbyl.

The term "lower carboalkoxymethyl" or "lower hydrocarbyloxycarbonylmethyl" refers to hydrocarbyl —OC(O)CH$_2$— with the hydrocarbyl group containing ten or fewer carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or fewer carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl —O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

"Disulfide" refers to —S—S—.

"Thioester" refers to

"Thioether" refers to C—S—C.

"Ester" refers to $$\overset{O}{\underset{}{\parallel}}\\ RCOR$$

"Analyte" shall mean substance of natural or synthetic origin sought to be detected and/or measured, said substance having a specific binding partner capable of a specific interaction with said analyte.

"Ligand" shall mean a binding partner to a ligand receptor. A substance which, if detected may be used to infer the presence of an analyte in a sample, including, without limitation, haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefore, i.e., the ligand receptor of a ligand-receptor assay.

"Receptor" shall mean a receptor capable of binding ligand, typically an antibody, or a fragment thereof, but which may be another ligand, depending on assay design.

"Ligand-Receptor Assay" shall mean an assay for an analyte which may be detected by the formation of a complex between a ligand and a ligand receptor which is capable of a specific interaction with that ligand. Ligand-Receptor assays may be competitive or non-competitive, homogeneous or heterogeneous.

"Immunogen" shall mean a chemical or biochemical structure, determinant, antigen or portion thereof, which elicits an immune response, including, for example, polylysine, bovine serum albumin and keyhole limpid hemocyanin (KLH).

"Antigenic" shall mean a chemical or biochemical structure, determinant, antigen or portion thereof which is capable of inducing the formation of an antibody.

DETAILED DESCRIPTION OF THE PREFERRED EMBODIMENTS

Figure 1:
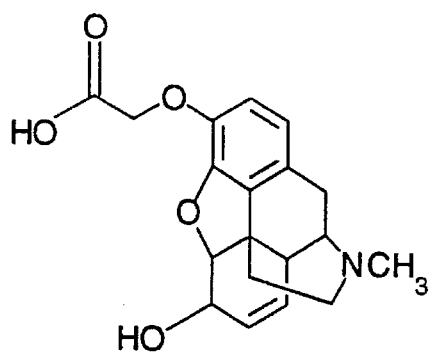
FIG. 1 depicts the structure of the compounds of Examples 2, and 3, which are 3'-0-Carboxymethylmorphine, 3-0-[2-(2- Amino-4-Thiolbutanoic Acid Thiolactone)-Acetamide-Morphine, and 3-0-[2-(Cysteine)-Acetamide]-Morphine, respectively.
Figure 1:
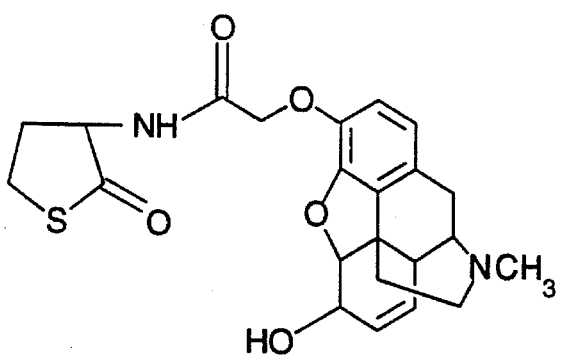
Figure 1:
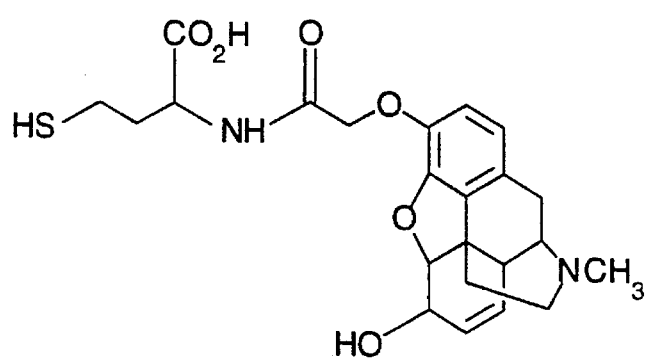
Figure 2:
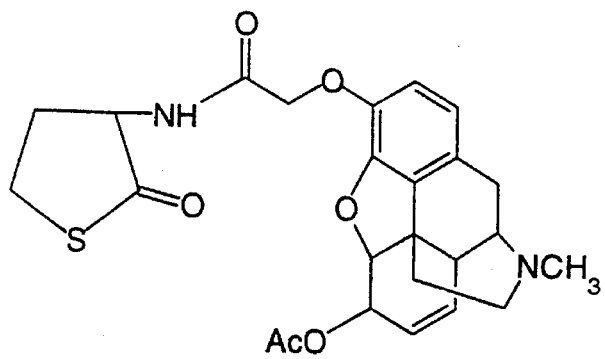
FIG. 2 depicts the structures of the compounds of Examples 4–7, which are 3-0-[2-(2-Amino-4-Thiolbutanoic Acid Thiolactone)Acetamide]-6-0-Acetyl Morphine, 3-0-[2- (Cysteine) Acetamide]-6-0-Acetyl Morphine, 6-0-Ethoxymorphine, and 6-0-Ethoxy-nor-Morphine, respectively.
Figure 2:
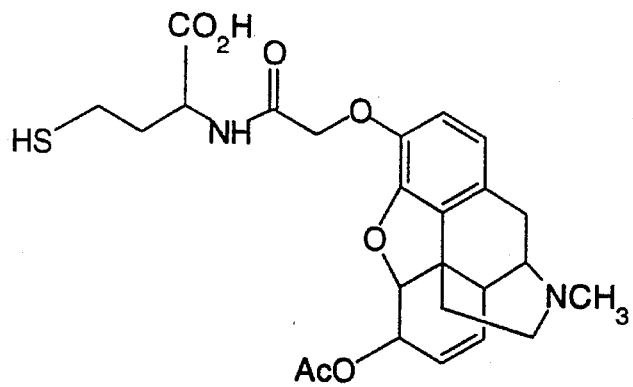
Figure 2:
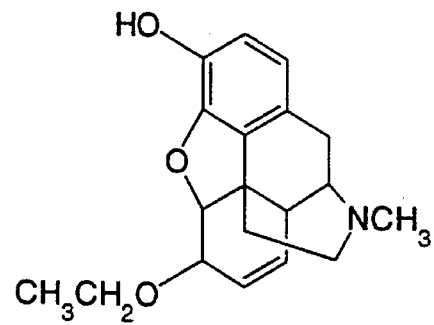
Figure 2:
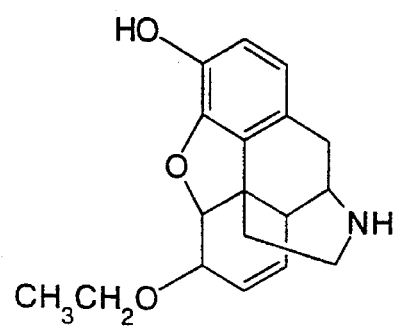
Figure 3:
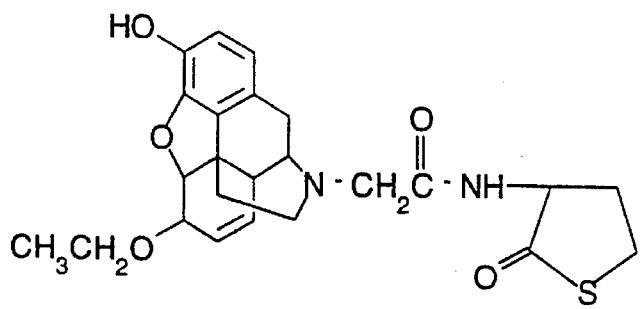
FIG. 3 depicts the structures of the compounds of Examples 9–12, which are 6-0-Ethoxy-N-[2-(2-Amino-4-Thiolbutanoic Acid Thiolactone)-Acetamide]-Morphine, 6-0-Ethoxy-N-[2-(Cysteine)Acetamide]-Morphine, 3-0-[2-(2-Amino-4-Thiobutoanic Acid Thiolactone)-Acetamide]-6-0-Ethoxy Morphine, and 3-0-[2-(Cysteine)-Acetamide]-6-0-Ethoxy-Morphine, respectively.
Figure 3:
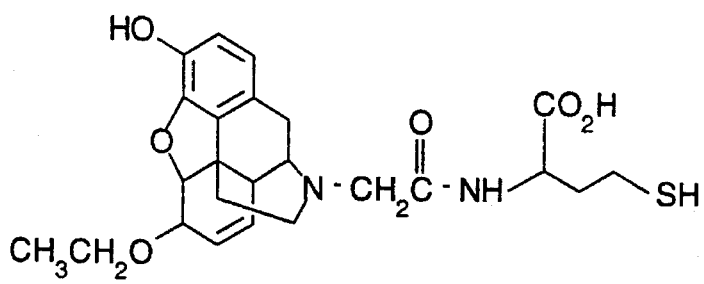
Figure 3:
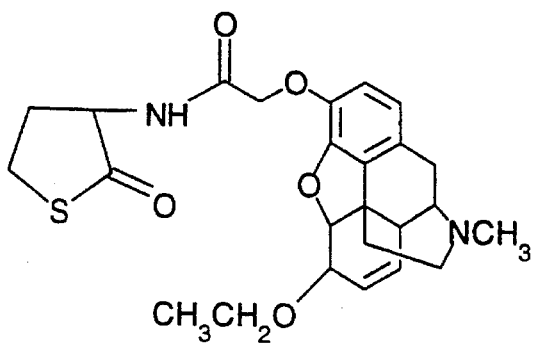
Figure 3:
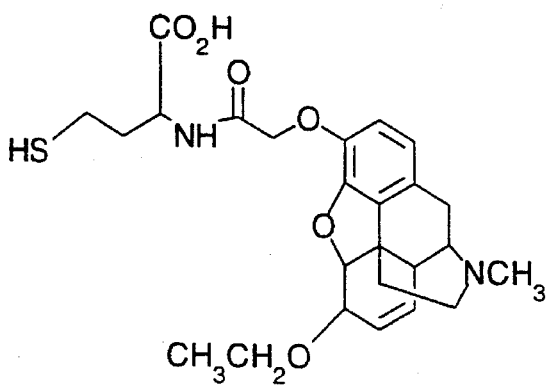
Figure 4:
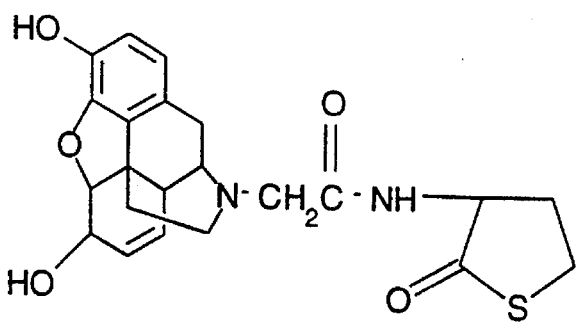
FIG. 4 depicts the structures of the compounds of Examples 13–16, which are N-[2-(2-Amino-4-Thiolbutanoic Acid Thiolactone)Acetamide]-Morphine, N-[2-(Cysteine)]Acetamide-Morphine, 6-0-Acetyl-N-[2[(2-Amino-4-Thiolbutanoic Acid Thiolactone)Acetamide]-Morphine, and 6-0-Acetyl-N-[(2-Cysteine)-Acetamide]Morphine, respectively.
Figure 4:
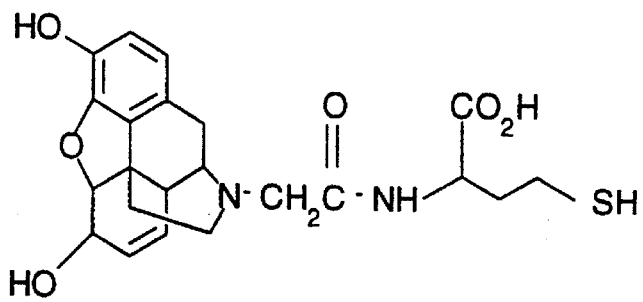
Figure 4:
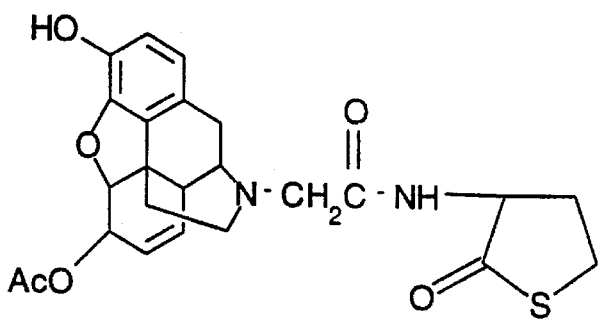
Figure 4:
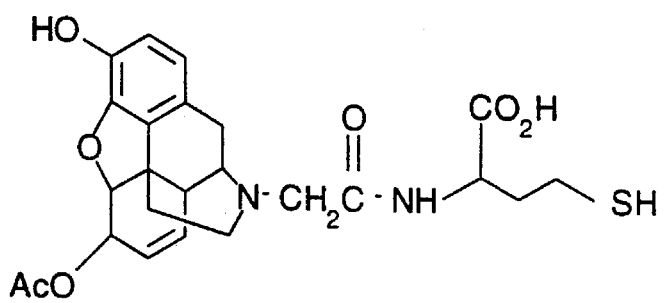

Novel compounds are described which are used in the generation of antibodies and in the immunoassay process generally. The compounds are derivatives of morphine and morphine metabolites. The derivatization of the opiate or opiate analogue for covalent attachment to proteins, polypeptides and labels occurs at the 3'-hydroxyl or at the nitrogen of nor-morphine or the nor-morphine analogues. The synthesis of the linking group between the protein, polypeptide or label and the opiate derivative is designed to achieve the derived binding of the drug derivative and the receptor. For example, the derivative may be displaced from the surface of the protein, polypeptide or label to allow the derivative to present itself to the binding domain of receptors.

In general, the compounds of this invention have the following formula:

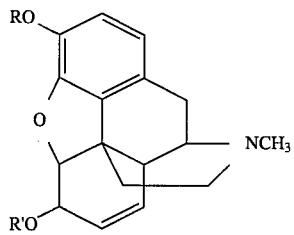

where R' is a linking group comprising one of the following:

—H, —CH₃,

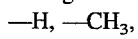

—CH₂CH₃
where R is

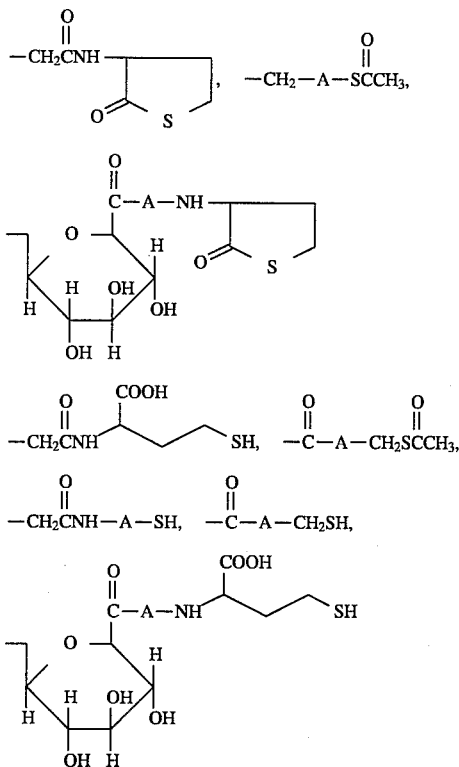

-continued

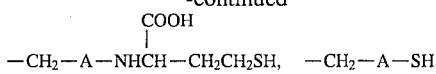

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label to a compound of the formula is of the following:

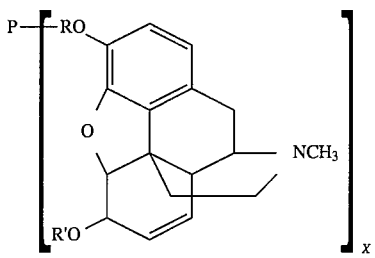

where P is an antigenic protein or polypeptide or a protein, polypeptide or label;
where x is at least one and not greater than 100;
where R' is
—H, —CH$_3$,

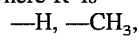

—CH$_2$CH$_3$ where R is a linking group comprising:

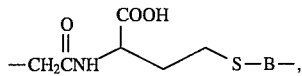

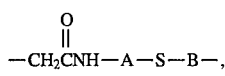

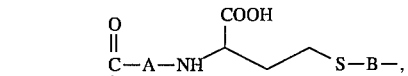

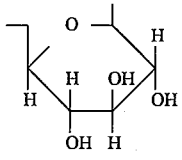

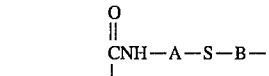

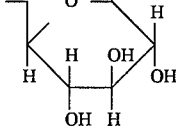

where A is a linking group of from 1 to 20 carbons and 0 to 10 heteroatoms (NH, O, S) either branched or straight chain;
where B is a linking group ultimately attached to a protein, polypeptide or label selected from the group comprising:

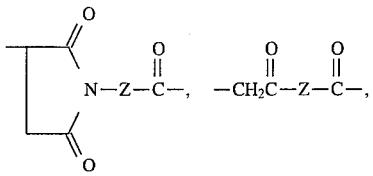

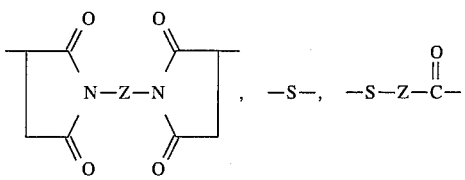

where Z is a linking group of from 1 to 20 carbons and 0 to 10 heteroatoms (NH, O, S) and may be branched or straight chain.

In addition, the general form of compounds of this invention can also have the following formula:
where R' is

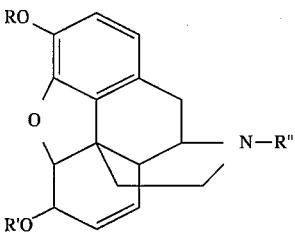

—H, —CH$_3$,

—CH$_2$CH$_3$
where R is H—,

CH$_3$CH$_2$—,

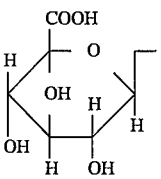

where R" is a linking group comprising:

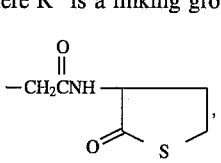

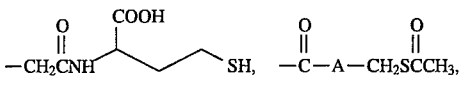

-continued

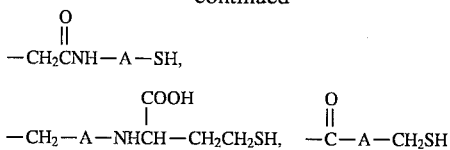

where A is a linking group of from 1 to 20 carbons and from 0 to 10 heteroatoms (NH, O, S), either branched or straight chain.

In addition, the general form of the immunogenic protein or polypeptide molecule or the protein or polypeptide molecule or label derivatized via an amide, disulfide, thioether, or ester bond to the molecule or label also to a compound of the formula is of the following:

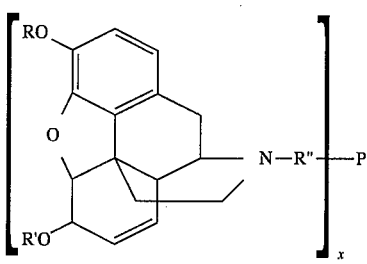

where P is an antigenic protein or polypeptide or a protein, polypeptide or label;

where x is at least one and not greater than 100;

where R' is

—H, —CH$_3$,

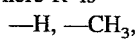

—CH$_2$CH$_3$ where R is

where R" is a linking group comprising:

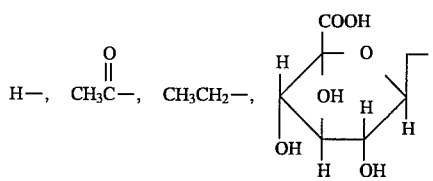

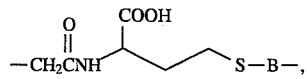

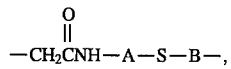

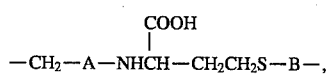

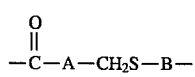

where A is a linking group of from 1 to 20 carbons and 0 to 10 heteroatoms (NH, O, S) either branched or straight chain;

where B is a linking group ultimately attached to a protein, polypeptide or label selected from the group consisting of:

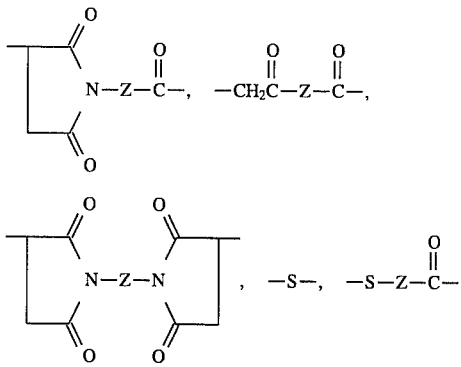

where Z is a linking group of from 1 to 20 carbons and 0 to 10 heterocarbons (NH, O, S) and may be branched or straight chain.

The particularly preferred (best mode) compounds of this invention have the following formula:

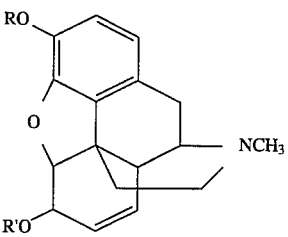

where R' is:
—H,

CH$_3$CH$_2$— where R is a linking group consisting of:

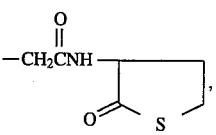

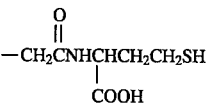

The particularly preferred (best mode) immunogenic protein or polypeptide molecule or the protein or polypeptide molecule or label derivatized via an amide or ester bond to the molecule or label to a compound of the formula is of the following:

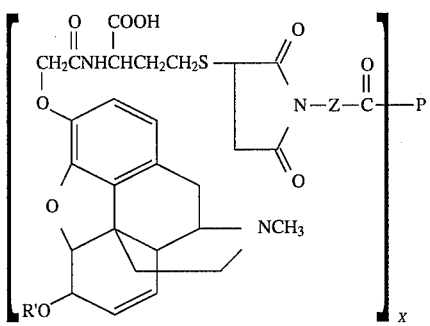

where P is an antigenic protein or polypeptide or a protein, polypeptide or label;
where x is at least one and not greater than 100;
where R' is
—H,

$CH_3CH_2$— where Z is a linking group of from 1 to 20 carbons and 0 to 10 heteroatoms (NH, O, S) and may be branched or straight chain.

The particularly preferred (best mode) compounds of this invention can also have the following formula:

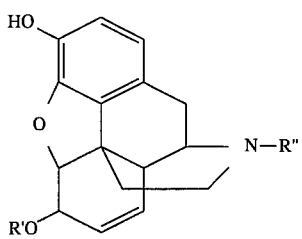

where R' is
—H,

$CH_3CH_2$— where R is a linking group comprising:

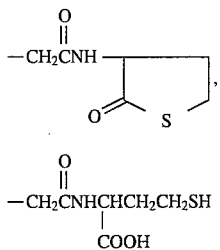

Also in addition, the particularly preferred (best mode) immunogenic protein or polypeptide molecule or the protein or polypeptide molecule or label derivatized via an amide or ester bond to the molecule or label to a compound of the formula is of the following:

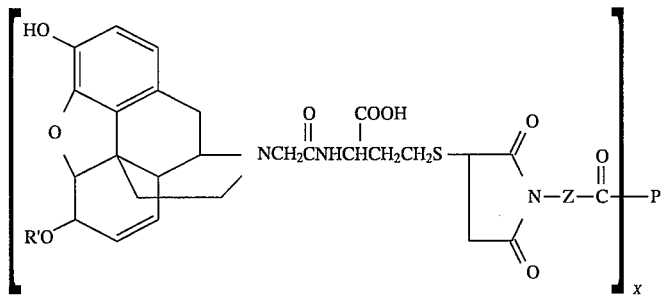

where P is an antigenic protein or polypeptide or a protein, polypeptide or label;
where x is at least one and not greater than 100;
where R' is
—H,

$CH_3CH_2$— where Z is a linking group of from 1 to 20 carbons and 0 to 10 heteroatoms (NH, O, S) and may be branched or straight chain.

Of particular interest are opiate derivatives where either or both of the 3'- and 6'- acetyl esters are changed to the respective ethoxy derivatives. These ether opiate derivatives are preferred to their ester counterparts because the ether moiety is much less susceptible to hydrolysis in aqueous solutions than the ester group. In addition, for the purposes of synthesizing a compound which mimics the structure of the metabolite to be measured, the ethyl ether moiety approximates the size of the acetyl ester group which is on the 3'- and 6'- positions of heroin. In the metabolism of heroin, the 3'-acetyl is first hydrolyzed to the 3'-hydroxyl group to form 6'-acetylmorphine (see J. Anal. Tox. 15, 1–7 (1991)). The 6'-acetylmorphine is further metabolized to morphine. Thus, a method to monitor heroin abuse requires the preparation of antibodies to 6'-acetylmorphine. However, the 6'-acetyl group is prone to hydrolysis in aqueous solutions. In addition, if a highly specific antibody to 6'-acetylmorphine is required then immunizing with an antigenic 6'-acetylmorphine conjugate may not result in high specificity antibodies to 6'-acetylmorphine because the 6'-acetyl ester of the opiate derivative on the immunogen is further metabolized in the animal during immunization or is simply hydrolyzed non-enzymatically to the respective morphine derivative. The 6'-ethoxymorphine derivative was synthesized to overcome this limitation so that antibodies could be raised to the stable 6'-ethoxymorphine derivative which in turn mimics the structure of 6'-acetylmorphine.

The compounds of the present invention are synthesized as thiols or thiol esters so that their covalent attachment to proteins, polypeptides or labels can easily be performed under mild conditions, for example, pH 7 in a protein solution. The linking group between the drug derivative and the thiol or thiol ester can be of various lengths. For example, the 3-hydroxy group of morphine or the secondary nitrogen of nor-morphine can be directly reacted with varying chain lengths of an alkyl halide carboxylic acid, for example, 4-bromobutyric acid and subsequently with an amino thiol ester, such as homocysteine thiolactone. Also, the aforementioned functional groups can be reacted with varying chain lengths of a carboxylic acid thiol ester, such as acetylthiopropionic acid. The thiol esters of the resulting derivative are hydrolyzed in dilute base, for example, 0.01M–0.1M potassium hydroxide, to generate the thiol group which is reacted with the thiol reactive group, such as a maleimide, an alkyl halide or a thiol. The thiol reactive group is generally on the protein, polypeptide or label but can also be incorporated onto the protein, polypeptide or label after the thiol drug reacts with the thiol reactive compound.

The protein, polypeptide or label is reacted with a reagent which incorporates a maleimide or alkylhalide into the molecule. These reagents and methods for their use are available from Pierce, Rockford, IL, for example, for incorporation of maleimide groups onto proteins, polypeptides or labels one can use succinimidyl 4-(N-maleimidomethyl)cyclohexane-1-carboxylate (SMCC), succinimidyl 4-(p-maleimidophenyl)butyrate (SMPB) or m-maleimidobenzoyl-N-hydroxysuccinimide ester (MBS). For introduction of an alkyl halide into a protein, polypeptide or label one can use N-succinimidyl(4-iodoacetyl)aminobenzoate (SIAB) also from Pierce. The thiol reactive group, such as maleimide, an alkyl halide or a thiol can be incorporated into the protein, polypeptide or label prior to reaction with the drug thiol, but the drug thiol can also be reacted with the thiol reactive compound prior to reaction with the protein, polypeptide or label. Also, bismaleimide compounds of varying length can be reacted with thiol containing proteins, polypeptides or labels for covalent coupling of the opiate thiol derivatives. Conversely, the bis-maleimide compound can be reacted with the thiol derivative and subsequently to the thiol containing protein, polypeptide or label. Common bis-maleimides are bis-maleimidohexane from Pierce, N,N'-bis (3-maleimidopropionyl)-2-hydroxy-1,3-propanediamine from Sigma Chemical Co., St. Louis, Mo., and 1,1'-(methylenedi-4,1-phenylene)-bismaleimide from Aldrich Chem. Co., Milwaukee, Wis. The thiol opiate derivatives can also form disulfides with a thiol containing polypeptide, protein or label molecules as a means to incorporate the derivative into the molecule.

Examples of the use of drug derivatives, immunogens and protein and polypeptide conjugates for generating antibodies and for use in the immunoassay process are described, for example, in U.S. Pat. Nos. 5,028,535 and 5,089,391.

EXPERIMENTAL EXAMPLES

Example 1

Synthesis of 3'-O-Carboxymethylmorphine Hydrochloride

Morphine sulfate (2.0 g, $6\times10^{-3}$ mol) and potassium carbonate (3 g, $2.2\times10^{-2}$ mol) were added to 100 ml of ethyl alcohol. Bromoacetic acid (1.0 g, $7.2\times10^{-3}$ mol) was added and the solution was refluxed with stirring for 2 h. The solution was allowed to cool to room temperature and 3.0 ml of hydrochloric acid (37%) was added. The solution was refluxed for 10 min. The solution was allowed to cool to room temperature and the solvent was removed in vacuo. Acetone (80 ml) was added to the residue and the suspension was stirred for 10 min. The precipitate was filtered and washed with 20 ml acetone. The filtrate was evaporated in vacuo. Hydrochloric acid (6N, 50 ml) was added to the residue and the solution was stirred at room temperature for 2 h. The solvent was removed in vacuo, water (40 ml) was added to dissolve the residue and the solvent was removed in vacuo. The water addition and evaporation in vacuo was repeated 2 times more. Acetone (50 ml) was added to the residue and the suspension was stirred until the oil solidified. The acetone was decanted. Acetone (90 ml) was added, decanted and acetone (90 ml) was again added to the residue. The precipitate in the acetone slurry was crushed with a glass rod and the suspension was filtered. The precipitate was washed with 10 ml acetone and was dried in vacuo. The recovered product, 3'-O-Carboxymethylmorphine hydrochloride, weighed 1.89 g.

Example 2

Synthesis of 3-O-[2-(2-Amino-4-Thiolbutanoic Acid Thiolactone)-Acetamide]-Morphine Hydrochloride (Morphine-HCTL)

3'-O-Carboxymethylmorphine hydrochloride (1.89 g, $5\times10^{-3}$ mol), dl-homocysteine thiolactone hydrochloride (0.75 g, $4.9\times10^{-3}$ mol) and pyridine (1.2 ml, $1.5\times10^{-2}$ mol) were dissolved in 30 ml anhydrous dimethylformamide. 1-(3-dimethylaminopropyl)-3-ethylcarbodiimide hydrochloride (1.1 g, $5.7\times10^{-3}$ mol) was added and the solution was stirred under argon at room temperature for 1 h. The solvents were removed in vacuo and water (80 ml) was added to the residue. The aqueous solution was extracted 2 times with a total of 100 ml methylene chloride. Saturated sodium carbonate solution (1 ml) was added to the aqueous phase to achieve a pH of 7. The aqueous solution was extracted 3 times with chloroform (300 ml) and the combined chloroform phases were extracted with water (80 ml).

The chloroform was dried with 6 g magnesium sulfate and filtered. The chloroform was removed in vacuo and the residue was triturated 3 times with water (300 ml). Ethyl alcohol (100 ml) was added to dissolve the residue and was removed in vacuo; this procedure was repeated 2 times. Methylene chloride (300 ml) was added to the residue and the suspension was stirred for 4 hours and then filtered. The methylene chloride was removed in vacuo and ethyl acetate (60 ml) was added to the flask and the residue was dissolved. Hydrogen chloride (1M) in diethyl ether (3 ml) was added to the solution and a white precipitate was formed. The precipitate was filtered and was washed with ethyl acetate. The precipitate was dried in vacuo and 0.97 g of the title compound was recovered.

Example 3

Synthesis of
3-O-[2-(Cysteine)-Acetamide]-Morphine

3-O-[2-(2-Amino-4-Thiolbutanoic Acid Thiolactone)Acetamide]-Morphine (0.01 g, $2.1 \times 10^{-5}$ mol) was dissolved in 0.835 ml dimethylformamide/water (70/30, v/v). Potassium hydroxide (0.209 ml, 1N) was added and the solution sat at room temperature for 5 min. Potassium phosphate buffer (0.3 ml, 0.5M, pH 7), was immediately added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Example 4

Synthesis of 3-O-[2-(2-Amino-4-Thiolbutanoic Acid Thiolactone)-Acetamide]-6-O-Acetyl Morphine Hydrochloride (6-Ace-tylmorphine-HCTL)

Morphine-HCTL (24 mg, $5 \times 10^{-5}$ mol) was dissolved in glacial acetic acid (1 ml) and sulfuric acid (98%, 1 μl) was added. The reaction was heated at 50° C. for 4 days. The solvent was removed in vacuo and the white solid was dissolved in water and was purified on a 1×25 cm Vydac C18 column using a linear gradient of 20 mM potassium phosphate, pH 7, to 100% methanol over 50 min. at a flow rate of 2 ml/min. The product eluted at 25–32 min. The fractions were evaporated in vacuo and the residue was triturated with ethyl alcohol (5 ml), filtered and the filtrate was evaporated in vacuo to yield 15.5 mg of the title compound.

Example 5

Synthesis of
3-O-[2-(Cysteine)Acetamide]-6-O-Acetyl Morphine

6-Acetylmorphine-HCTL (0.3 mg, $4.8 \times 10^{-7}$ mol) was dissolved in 0.025 ml dimethylformamide/water (70/30, v/v). Potassium hydroxide (0.006 ml, 1N) was added and the solution sat at room temperature for 2 min. Potassium phosphate buffer (0.1 ml, 0.5M, pH 7), was immediately added. The title compound in solution was used as is to react with thiol reactive groups, such as maleimides, alkyl halides or thiols, which are either free in solution or are coupled to proteins, polypeptides or labels.

Example 6

Synthesis of 6-O-Ethoxymorphine

Morphine hydrate (1.42 g, $4.68 \times 10^{-3}$ mol) in anhydrous tetrahydrofuran (50 ml) was added dropwise over 20 min. to a stirring suspension, under argon and on an ice/water bath, of potassium hydride (1.75 g, $4.36 \times 10^{-2}$ mol) in anhydrous tetrahydrofuran (50 ml). The suspension was stirred for 6 h. under argon on an ice/water bath and then the suspension was allowed to warm to room temperature. Ethyl iodide (0.72 ml, $9 \times 10^{-3}$ mol) was added and the suspension was stirred under argon at room temperature for 1 h. The suspension was cooled on an ice/water bath and water (10 ml) was added dropwise to the suspension followed by hydrochloric acid (1N, 50 ml). The solvents were removed in vacuo, water (50 ml) was added to the residue and the suspension was filtered. The aqueous filtrate was extracted 2 times with chloroform (40 ml). The aqueous phase was then treated with hydrochlorid acid (6N, 5 ml) to achieve a pH of 7. The aqueous phase was then extracted 10 times with chloroform (400 ml). The combined chloroform phases were dried over magnesium sulfate, filtered and the solvent was removed in vacuo. The title compound was recovered (430 mg) as a pale brown glassy solid.

Example 7

Synthesis of 6-O-Ethoxy-nor-Morphine

6-O-Ethoxymorphine (0.13 g, $4 \times 10^{-4}$ mol) was dissolved in chloroform (10 ml) and potassium bicarbonate (0.61 g, $6 \times 10^{-3}$ mol) and phenyl chloroformate (0.35 ml, $2.8 \times 10^{-3}$ mol) were added. The solution was refluxed with stirring for 2 h. and then additional potassium bicarbonate (0.61 g, $6 \times 10^{-3}$ mol) and phenyl chloroformate (0.35 ml, $2.8 \times 10^{-3}$ mol) were added. The solution was refluxed an additional 2 h. The reaction mixture was cooled to room temperature, the solution filtered and the filtrate was evaporated in vacuo. The residual oil was gassed with argon, cooled on an ice/water bath and treated dropwise with allyl alcohol (0.44 ml, $6.4 \times 10^{-3}$ mol) followed by hydrazine (1.51 ml, $4.8 \times 10^{-2}$ mol). The solution was then refluxed under argon for 7 h. The solution was cooled to room temperature, water (1 ml) was added and the solvents were removed in vacuo. The residue was treated with hydrochloric acid (2N) until the pH was 3. The aqueous solution was extracted 2 times with diethyl ether (20 ml). Ammonium hydroxide (30%) was added to the aqueous phase to pH 9 and the solution was extracted 3 times with chloroform (60 ml). The combined chloroform extracts were dried over magnesium sulfate, filtered and evaporated in vacuo to yield 101 mg of the title compound.

Example 8

Synthesis of 2-(2-Amino-4-Thiolbutanoic Acid Thiolactone)Bromoacetamide (Bromoacetyl-HCTL)

Bromoacetic acid (1.0 g, $7.2 \times 10^{-3}$ mol), dl-homocysteine thiolactone hydrochloride (1.1 g, $7.2 \times 10^{-3}$ mol) and pyridine (1.2 ml, $1.5 \times 10^{-2}$ mol) were dissolved in anhydrous dimethylformamide (36 ml) and then 1-(3-dimethylaminopropyl)-3-ethylcarbodiimide hydrochloride (1.52 g, 7.9×10⁻³ mol) was added. The reaction was stirred at room temperature for 18 h. The solvents were removed in vacuo and ethanol (10 ml) was added to dissolve the residue and then the ethanol was removed in vacuo. Ethanol (10 ml) was again added to dissolve the residue and was removed in vacuo. Water (20 ml) was added to the oil and the aqueous solution was extracted 3 times with methylene chloride (45 ml). The combined organic extracts were dried over anhydrous magnesium sulfate. The solution was filtered and the solvent was removed in vacuo to give a clear oil. Diethyl ether (5 ml) was added and the resulting precipitate was collected and washed on a fritted funnel. The precipitate was dried in vacuo and 1.0 g of the title compound was recovered.

Example 9

Synthesis of
6-O-Ethoxy-N-[2-(2-Amino-4-Thiolbutanoic Acid
Thiolactone)-Acetamide]-Morphine Hydrochloride
(6-Ethoxy-N-HCTL-Morphine)

6-Ethoxy-nor-morphine (0.1 g, $3.3\times10^{-4}$ mol) and bromoacetyl-HCTL (0.083 g, $3.5\times10^{-4}$ mol) were dissolved in anhydrous dimethylformamide (3 ml). Potassium carbonate (0.055 g, $4\times10^{-4}$ mol) was added and the solution was stirred at room temperature for 23 h. The solvent was removed in vacuo and the residue was triturated with ethyl acetate and filtered. The filtrate was acidified with hydrochloric acid (1N) in diethyl ether to pH 2. The white precipitate was collected on a fritted funnel and dried in vacuo. The recovery of the title compound was 100 mg.

Example 10

Synthesis of
6-O-Ethoxy-N-[2-(Cysteine)-Acetamide]-Morphine

6-Ethoxy-N-HCTL-morphine (10 mg, $2\times10^{-5}$ mol) was dissolved in 0.98 ml dimethylformamide/water (70/30, v/v). Potassium hydroxide (0.02 ml, 10N) was added and the solution sat at room temperature for 5 min. Potassium phosphate buffer (0.2 ml, 0.5M, pH 7), was immediately added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Example 11

Synthesis of 3-O-[2-(2-Amino-4-Thiolbutanoic Acid
Thiolactone)-Acetamide]-6-O-Ethoxy-Morphine
Hydrochloride (6-Ethoxy-Morphine-HCTL)

6-O-Ethoxymorphine (0.13 g, $4\times10^{-4}$ mol), bromoacetyl-HCTL (0.19 g, $8\times10^{-4}$ mol) and powdered potassium carbonate (0.11 g, $8\times10^{4}$ mol) were added to anhydrous dimethylformamide (4 ml) and the solution was stirred under argon, at room temperature for 21 h. The solvent was removed in vacuo and the residue was triturated twice with ethyl acetate (30 ml). The ethyl acetate solution was extracted 4 times with water (30 ml), dried over anhydrous magnesium sulfate and filtered. The ethyl acetate was removed in vacuo and again dissolved in ethyl acetate (15 ml) and acidified with hydrochloric acid (1M) in ethyl ether to pH 2. A beige solid precipitated and was filtered and washed with ethyl acetate. The crude product was dissolved in water (0.8 ml) and was purified on a Vydac 1×25 cm, reversed phase C18 column using a linear gradient of 20 mM potassium phosphate, pH 7 to 100% methanol over 80 min. at a flow rate of 2 ml/min. The product eluted between 52–55 min. and the fractions were combined and the solvents removed in vacuo. The residue was triturated with ethanol (100%, 20 ml) and filtered. The ethanol was removed in vacuo and the residue was triturated twice with ethyl acetate (10 ml) and the combined organic solutions were acidified with hydrochloric acid (1M) in ethyl ether to pH 2. The solvents were removed in vacuo and the product was dried in vacuo. The title compound (12 mg) was recovered as an off-white solid.

Example 12

Synthesis of
3-O-[2-(Cysteine)-Acetamide]-6-O-Ethoxy-Morphine

6-Ethoxymorphine-HCTL (0.01 g, $2\times10^{-5}$ mol) was dissolved in 1 ml dimethylformamide/water (80/20, v/v). Potassium hydroxide (0.02 ml, 10N) was added and the solution sat at room temperature for 30 sec. Potassium phosphate buffer (0.3 ml, 0.5M, pH 7), was immediately added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Example 13

Synthesis of N-[2-(2-Amino-4-Thiolbutanoic Acid
Thiolactone)-Acetamide]-Morphine Hydrochloride
(N-HCTL-Morphine)

nor-Morphine (0.3 g, $1\times10^{-3}$ mol) and bromoacetyl-HCTL (0.248 g, $1.04\times10^{-3}$ mol) were dissolved in dimethylformamide (10 ml) and then anhydrous potassium carbonate (0.15 g, $1.1\times10^{-3}$ mol) was added. The reaction was stirred at 50° C. for 24 h. The solution was filtered and the solvent was removed in vacuo. The yellow oil was triturated with methylene chloride (20 ml) and the precipitate was filtered and washed with methylene chloride. The compound was dried in vacuo and 0.25 g of the title compound was recovered.

Example 14

Synthesis of N-[2-(Cysteine)]Acetamide-Morphine

N-HCTL-morphine (9.3 mg, $2\times10^{-5}$ mol) was dissolved in 0.98 ml dimethylformamide/water (70/30, v/v). Potassium hydroxide (0.02 ml, 10N) was added and the solution sat at room temperature for 2 min. Potassium phosphate buffer (0.2 ml, 0.5M, pH 7), was immediately added and the solution was adjusted to pH 7–7.5 with hydrochloric acid (1N). The title compound in solution was used as is to react with thiol reactive groups, such as maleimides, alkyl halides or thiols, which are either free in solution or are coupled to proteins, polypeptides or labels.

Example 15

Synthesis of
6-O-Acetyl-N-[2-(2-Amino-4-Thiolbutanoic Acid
Thiolactone)-Acetamide]-Morphine Hydrochloride
(6-Acetyl-N-HCTL-Morphine)

N-HCTL-morphine (0.12 g, $2.6 \times 10^{-4}$ mol) was dissolved in glacial acetic acid (3.6 ml) and then sulfuric acid (0.013 ml, 95%) was added. The solution was stirred and heated at 70° C. for 6 days. The solvent was removed in vacuo and 25 mg of the residue was dissolved in 0.1M potassium phosphate, pH 3/methanol (0.25 ml, 50/50, v/v) and purified on a Vydac reverse phase C18 column (1×25 cm) equilibrated in 20 mM potassium phosphate, pH 4.6 at 2 ml/min. The product was eluted with a gradient of up to 60% methanol in 54 min. The title compound eluted between 52 and 58 min. The fractions were pooled, the solvent removed in vacuo and the residue was triturated with ethanol (10 ml). The ethanol solution was filtered and the solvent was removed in vacuo to yield 9.1 mg of the title compound.

Example 16

Synthesis of
6-O-Acetyl-N-[(2-Cysteine)-Acetamide]Morphine

6-Acetyl-N-HCTL morphine (0.7 mg, $1.4 \times 10^{-6}$ mol) was dissolved in 0.07 ml dimethylformamide/water (70/30, v/v). Potassium hydroxide (0.017 ml, 1N) was added and the solution sat at room temperature for 2 min. Potassium phosphate buffer (0.25 ml, 0.5M, pH 7), was immediately added. The title compound in solution was used as is to react with thiol reactive groups, such as maleimides, alkyl halides or thiols, which are either free in solution or are coupled to proteins, polypeptides or labels.

Other embodiments are within the following claims.

I claim:

1. A compound of the formula:

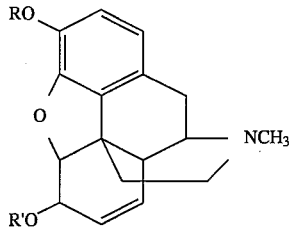

where R' is selected from the group consisting of:
—H, —CH$_3$,

—CH$_2$CH$_3$ where R is a linking group selected from the group consisting of:

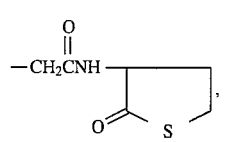

and

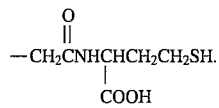

2. An immunogenic protein or polypeptide molecule or a protein or polypeptide molecule or a label derivatized to a compound of the formula:

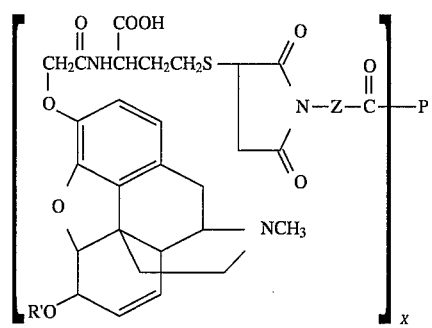

where P is an antigenic protein or polypeptide or a protein, polypeptide or label;

where x is at least one and not greater than 100;

where R' is selected from the group consisting of:
—H, —CH$_3$,

—CH$_2$CH$_3$ where Z is a linking hydrocarbyl group of from 1 to 20 carbons and from 0 to 10 heteroatoms selected from the group consisting of nitrogen, oxygen, and sulfur, which may either be in the chain or substituted on the chain which may be straight or branched.

3. A compound of the formula:

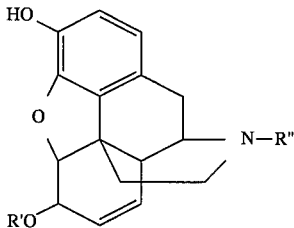

where R' is selected from the group consisting of:
—H, —CH$_3$,

and —CH$_2$CH$_3$ where R" is a linking group selected from the group consisting of:

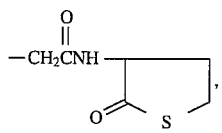

and

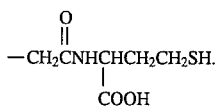

4. A compound of the formula:

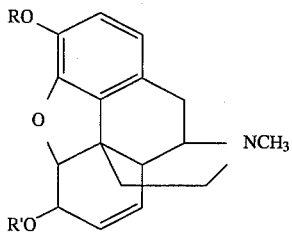

where R is a linking group selected from the group consisting of:

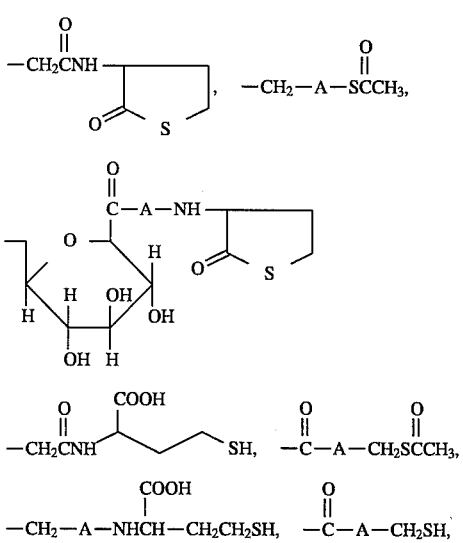

and

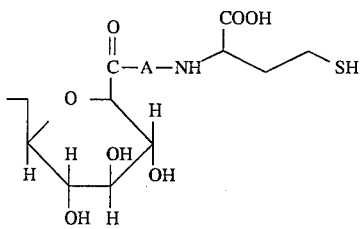

where R' is a member of the group consisting of:
—H, —CH₃, $$-\overset{O}{\underset{\|}{C}}CH_3,$$

and —CH₂CH₃ where A is a linking hydrocarbyl group of from 1 to 20 carbons and from 0 to 10 heteratoms selected from the group consisting of nitrogen, oxygen, and sulfur, which may either be in the chain or substituted on the chain which may be straight or branched.

5. An immunogenic protein or polypeptide molecule or a protein or polypeptide molecule or a label derivatized to a compound of the formula:

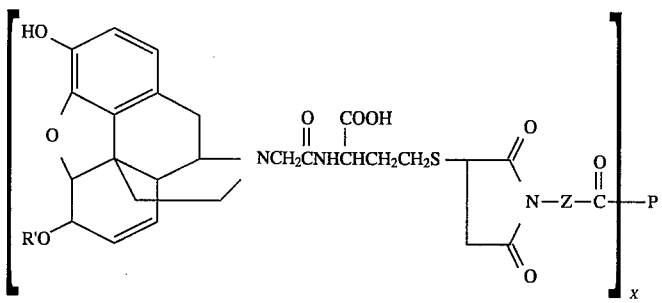

where P is an antigenic protein or polypeptide or a protein, polypeptide or label;

where x is at least one and not greater than 100;

where R' is selected from the group consisting of:
—H, —CH₃, $$-\overset{O}{\underset{\|}{C}}CH_3,$$

and —CH₂CH₃ where Z is a linking hydrocarbyl group of from 1 to 20 carbons and from 0 to 10 heteroatoms selected from the group consisting of nitrogen, oxygen, and sulfur, which may either be in the chain or substituted on the chain which may be straight or branched.

* * * * *